(12) United States Patent
Klein

(10) Patent No.: US 6,197,317 B1
(45) Date of Patent: *Mar. 6, 2001

(54) COMPOSITION AND METHOD FOR THE TREATMENT OF SKIN

(76) Inventor: Marvin E. Klein, 27629 Chatsworth St., Farmington Hills, MI (US) 48334

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/098,264

(22) Filed: Jun. 16, 1998

Related U.S. Application Data

(60) Provisional application No. 60/073,977, filed on Feb. 6, 1998, and provisional application No. 60/055,405, filed on Aug. 11, 1997.

(51) Int. Cl.$^7$ ...................................................... A61K 7/00
(52) U.S. Cl. ........................ 424/401; 514/561; 514/846; 514/944
(58) Field of Search ............................. 424/401; 514/561, 514/846, 944

(56) References Cited

U.S. PATENT DOCUMENTS

| | | | |
|---|---|---|---|
| 4,105,782 | 8/1978 | Yu et al. | 424/283 |
| 4,105,783 | 8/1978 | Yu et al. | 424/283 |
| 4,419,343 | 12/1983 | Pauly | 424/59 |
| 4,707,354 | 11/1987 | Garlen et al. | 424/47 |
| 4,983,382 | 1/1991 | Wilmott et al. | 424/62 |
| 5,091,171 | 2/1992 | Yu et al. | 424/642 |
| 5,140,043 | 8/1992 | Darr et al. | 514/474 |
| 5,478,560 | 12/1995 | Tominaga et al. | 424/401 |
| 5,720,949 | * 2/1998 | Davis . | |

FOREIGN PATENT DOCUMENTS

96/19182    6/1996  (WO) .

OTHER PUBLICATIONS

Derwent Abstract, Accession No. 1990–239996. German Patent DE 3905299. 1990.*

* cited by examiner

Primary Examiner—Diana Dudash
Assistant Examiner—Alysia Berman
(74) Attorney, Agent, or Firm—Gifford, Krass, Groh, Sprinkle, Anderson & Citkowski, P.C.

(57) ABSTRACT

A composition for the treatment of skin includes an alpha amino acid, which is most preferably an alpha amino dicarboxylic acid such as aspartic acid or glutamic acid. The composition has a pH in the range of 0.5 to 5. Also disclosed is a method for preparing the compositions wherein the amino acid is first solubilized in a strong acid, and the resultant solution then neutralized with a base to the therapeutic pH range. Also disclosed is a carrier for dermatological compositions comprising a solution of ascorbic acid and mineral salts.

9 Claims, No Drawings

COMPOSITION AND METHOD FOR THE TREATMENT OF SKIN

RELATED APPLICATIONS

This patent application claims priority of provisional patent application Ser. No. 60/073,977 filed Feb. 6, 1998 and entitled "Composition and Method for the Treatment of Skin," and of provisional patent application Ser. No. 60/055,405 filed Aug. 11, 1997 and entitled "Stabilized Composition for the Treatment of Skin."

FIELD OF THE INVENTION

This invention relates generally to dermatological compositions and methods for their use. More specifically, the invention relates to dermatological compositions based upon alpha amino acids. Most specifically, this invention relates to dermatological compositions based upon alpha amino acids having a pH in the range of 0.5 to 5.

BACKGROUND OF THE INVENTION

A large variety of materials and compositions have been employed for the topical treatment of skin conditions caused by drying, photodamage, aging, acne and the like. In addition to being effective and safe, any product used for the treatment of skin conditions should be convenient to formulate, easy to use, have long term stability, and be easy to handle. Additionally, such products should preferably be low in cost.

Retinoic acid, and other retinoid compounds are effective for treating acne, wrinkles and other skin conditions. However, these materials can be very toxic and must be used under close medical supervision, and hence are prescription medications. In addition, retinoids are expensive. Strongly corrosive materials such as phenol, mineral acids and halocarboxylic acids such as trichloroacetic acid have been used to treat damaged skin by peeling away the outer layers. These materials must also be used under medical supervision since they can produce serious damage if misapplied.

A number of formulations have been developed for dermatological preparations using alpha hydroxy acids and alpha keto acids. These acids are used at fairly high concentrations, in clinical settings, to produce superficial peeling of the skin. They are also used at lower concentrations by consumers and paraprofessionals to smooth and condition the skin and reduce wrinkles. In many instances, these materials can still be irritating, and as a result compositions have been developed wherein buffering agents such as amphoteric compounds or alkaline materials have been added to the acids to raise their pH. Such compositions are shown in U.S. Pat. Nos. 4,105,782; 4,105,783 and 5,091,171. In other instances, skin care compositions have been formulated utilizing ascorbic acid, and such compositions are shown in U.S. Pat. Nos. 4,983,382 and 5,140,043.

In yet other instances, skin care compositions have been prepared utilizing relatively neutral species such as salts. PCT Patent Application WO96/19182 discloses the use of inorganic salts, primarily of magnesium, manganese and various lanthanide elements for reducing skin irritation. U.S. Pat. No. 5,478,560 discloses the use of salts of mixed amines for treating dry skin.

As can be seen, there is a very large body of prior art directed to topical treatments for various dermatological conditions. The efficacy and safety of the various prior art compositions vary widely as do the cost and ease of formulating and using the compositions. Thus, there is still a need for a composition for treating dermatological conditions, which composition is effective, safe, easy to formulate and use and low in cost. As will be described hereinbelow, the present invention provides a composition which has very good utility for treating skin conditions associated with dryness, aging, photodamage such as photopigmentation and keratoses as well as acne and seborrheic keratoses. These and other advantages of the present invention will be apparent from the discussion and description which follow.

BRIEF DESCRIPTION OF THE INVENTION

There is disclosed herein a composition for the treatment of skin. The composition is based upon alpha amino acids and has a pH in the range of 0.5 to 5. Some of the preferred acids comprise alpha amino dicarboxylic acids, with aspartic and glutamic acid being some particularly preferred acids. In particular embodiments of the invention, the compositions further include a strong acid which functions to solubilize the alpha amino acid, and the composition may further include a basic material for the purpose of adjusting the pH to the preferred range of 0.5 to 5. The compositions of the present invention may also include ascorbic acid as well as inorganic salts, which most preferably comprise a mixture of salts obtained from the Dead Sea.

The present invention also concerns a method for formulating the therapeutic compositions, and in accord with the method, an alpha amino acid is dissolved in a solvent system which includes a strong acid, and this strong acid is neutralized so as to adjust the pH of the solution to the preferred range of 0.5 to 5. Also within the scope of the present invention is a method for treating skin which comprises applying the compositions of the present invention to the skin. The present invention also is directed to a base for a dermatological composition which comprises ascorbic acid and a mixture of inorganic salts of alkali and/or alkaline metals in a carrier. The base may further include urea.

DETAILED DESCRIPTION OF THE INVENTION

In accord with one aspect of the present invention, it has been found that certain amino acids have a very beneficial therapeutic effect on the skin. The compositions of the present invention improve the tone and texture of the skin and decrease wrinkling due to drying and aging. The compositions also decrease photodamage to the skin such as photopigmentation and solar keratoses, and the compositions also operate to remove or decrease the severity of acne and seborrheic keratoses. Among the preferred amino acids are the alpha amino acids and within the context of this disclosure it is to be understood that alpha amino acids are those acids in which the amine group is on the carbon which is alpha to the carboxylic acid moiety. In general, alpha amino acids have the formula set forth hereinbelow:

Formula 1

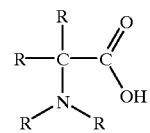

Wherein the R groups are independently alkyl, aryl, heterocycles, or hydrogen. It is believed that the alpha configuration results in a beneficial chemical interaction between the amino acid and the skin.

Among some of the most preferred alpha amino acids are the alpha amino dicarboxylic acids. As will be understood by those of skill in the chemical arts, alpha amino dicarboxylic acids are those amino acids having two carboxyl groups, and in which the amine group is alpha to at least one of the carboxyl groups. Two of the particularly preferred alpha amino dicarboxylic acids which may be employed in the practice of the present invention are aspartic acid, shown at Formula 2 hereinbelow, and glutamic acid, shown at Formula 3 hereinbelow.

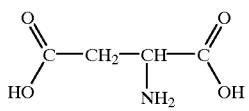

Formula 2

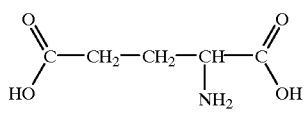

Formula 3

It is to be understood that these amino acids may be also present as salts or ions.

The materials of the present invention are of very low toxicity, and are relatively nonirritating to the skin; hence, they may be used in very high concentrations. However, it has been found that in most instances, amino acid concentrations ranging up to 20%, by weight, are generally effective. In those situations where the composition is being employed in a clinical setting, and particularly when keratoses and other such conditions are being addressed, relatively high concentrations of the composition will be employed. In those instances where the material is being utilized in a nonclinical setting and/or relatively minor conditions are being treated, lower concentrations will suffice. Typically, concentrations of amino acids in the range of 0.5–20% are employed, with concentrations in the range of 2–3% being sufficient for many treatment plans.

The amino acids of the present invention are disposed in a carrier, which in the simplest case comprises water. In other instances, water or alcohol based lotions as well as creams, ointments, gels and other such pharmaceutically acceptable carriers may be utilized. As is known in the art, carriers may further include fragrances, emollients, coloring agents, preservatives, and the like.

In some instances, the alpha amino acids of the present invention are of relatively low solubility in water, weak acids or alcohol. In addressing this problem, it has been found that further enhancements to the compositions of the present invention may be achieved if the alpha amino acid is first dissolved in a solvent system which includes a strong acid therein. As is known in the art, and within the context of this disclosure, strong acids are those acids which are highly ionized in solution and are generally categorized as having a dissociation constant ($K_A$) which is greater than 1. Trichloroacetic acid is one strong acid which is preferably employed in the practice of the present invention. Other strong acids comprise other halocarboxylic acids such as fluoroacetic acids as well as mineral acids such as hydrochloric acid, sulfuric acid, perchloric acid and the like.

In accord with this aspect of the present invention, the alpha amino acid is first dissolved in the solvent system which includes a strong acid therein. For example, it has been found that solutions of up to 20%, by weight, of trichloroacetic acid are highly effective solvents for aspartic acid, which is one of the particularly preferred alpha amino acids of the present invention. After the solution of the alpha amino acid is complete, at least a portion of the remaining strong acid in the solution is neutralized so as to raise the pH of the solution to a therapeutically preferred range. Typically, this range is from approximately 0.5 to approximately 5, and it has been found that the solubilized alpha amino acids remain in solution, in relatively high concentrations, at this pH range. In those instances where the composition of the present invention is being employed in a clinical setting, under professional supervision, relatively low pHs of 0.5 to 2.0 may be effectively employed. In those instances where compositions are being prepared for use in a home, or other nonprofessional setting, relatively higher pHs in the range of 2 to 3 are typically employed. In some instances, effective, stable compositions may be prepared having pHs as high as 5.

Neutralization of the acid may be carried out using any basic material which is compatible with the solvent system and physiologically acceptable. One particularly preferred base comprises urea, and it is believed that the urea, or any resultant salt of urea, further enhances the therapeutic effect of the composition. Other bases which may be advantageously employed are purines, as well as anines. Ammonium hydroxide may also be effectively employed as a base, as may be inorganic bases such as sodium hydroxide and other alkali metal hydroxides.

While not wishing to be bound by conjecture, the inventor speculates that it is possible that the strong acid solubilization and neutralization steps may produce new chemical species which further enhance the efficacy of the alpha amino acids of the present invention. Such enhancement may come from the formation of salts or from a chemical rearrangement of the amino acid, as for example by the addition of further carboxyl groups thereto, or by the formation of esters, imines, imides, amides and other such species.

In the broadest sense, the compositions of the present invention are based upon the use of therapeutic compositions of alpha amino acids, and more preferably alpha amino dicarboxylic acids. In yet more specific embodiments of the invention, the compositions are prepared by a method wherein strong acids are first employed to solubilize the alpha amino acids, and bases are then employed to adjust the pH of the resultant composition.

In accord with still other aspects of the present invention, yet other auxiliary ingredients may be added to the compositions. For example, it has been found that ascorbic acid further enhances the efficacy of the compositions. Most typically, the ascorbic acid, if employed, is present in an amount, by weight, of up to 5% of the composition, although higher concentrations such as 20% may be employed. While there is no lower limit to the amount of ascorbic acid which may be employed, typically, if it is employed at all, it is present in an amount of at least 0.5% by weight. In a most preferred embodiment of the invention, ascorbic acid comprises, by weight, 0.5–5% of the composition. In other instances, citric acid may be included in the compositions, in similar amounts. In yet other instances inorganic salts can be added to the composition, as will be elaborated upon hereinbelow.

Yet other auxiliary ingredients may be employed in the compositions of the present invention. For example, the compositions may be formulated into a cream, gel or lotion base, using any pharmaceutically acceptable carrier. In some instances, the compositions may be formulated into a peel-off mask by employing a film forming carrier such as polyvinyl alcohol or an inorganic, mud pack type carrier such as a clay-based material. As is known in the art, colorings, fragrances, preservatives and the like may be similarly included in the compositions of the present invention.

The following are some examples of compositions in accord with the present invention.

EXAMPLE 1

5 grams of L-aspartic acid was dissolved in the solvent system comprising 100 grams of a 20% aqueous solution of trichloroacetic acid, at room temperature. This produced a clear and complete solution having a pH of less than 1. Solid urea was slowly added to the solution until the pH rose to approximately 3. It was found that this resultant solution was stable and did not crystallize out on standing. The solution was found to have good therapeutic efficacy.

EXAMPLE 2

A second composition was prepared utilizing a portion of the stock material prepared in Example 1. In this example, 3%, by weight, of L-ascorbic acid was dissolved in the stock solution. The thus produced clear solution did not crystallize out on standing, and the pH of the resultant solution was approximately 3.0. The solution was stable on storage and had good therapeutic efficacy.

EXAMPLE 3

A further composition was prepared from the stock solution of Example 1 by dissolving, by weight, 2% citric acid therein. The resultant solution was storage stable, and had a pH of approximately 2.0, and manifested good therapeutic efficacy.

EXAMPLE 4

The stock solution of Example 1 was blended, on a 50% weight basis, with a conventional cold cream base to produce a cream composition. The resultant cream was storage stable and had good therapeutic efficacy.

Yet other compositions can be prepared in accord with the present invention. As discussed above, other alpha amino acids, such as glutamic acid, may be advantageously employed. Still other additives, such as mineral salts, may be employed in the compositions. One particularly preferred group of mineral salts comprises minerals of the type found in the Dead Sea, or synthetic equivalents thereof. These minerals include mixtures of salts of Group I and Group II elements. Most specifically, such Dead Sea minerals comprise mixtures of carbonates, bicarbonates, halides and sulfates of potassium, magnesium, calcium and sodium. Salts, in an amount of up to 5% by weight of the composition, may be advantageously included therein. In some instances, in which a strong acid is used to solubilize the amino acid, the salts themselves may function as bases for the neutralization of excess acid.

Yet other auxiliary materials may be added to the compositions of the present invention. For example, other organic acids, such as lactic acid, salicylic acid and the like may be included in the compositions. Other therapeutic materials such as cortisones or topical anesthetics may be included in the compositions.

The amino acid compositions of the present invention may be disposed in a variety of pharmaceutically acceptable carriers such as lotions, gels and the like as described hereinabove. In accord with yet another aspect of the present invention, it has been found that a carrier base may be advantageously prepared from a mixture of ascorbic acid and mineral salts, most preferably Dead Sea mineral salts as described hereinabove. In addition, the base may include urea. The base solubilizes and stabilizes the compositions of the present invention. While the base may be advantageously employed with the amino acid derived compositions of the present invention, it may also be employed with other dermatological compositions such as compositions based upon hydroxy acids, retinoids, inorganic materials and the like.

The base of the present invention further includes a vehicle, which in the simplest case may comprise water, or the vehicle may comprise lotion, cream, gel or ointment. It has been found that the ascorbic acid and salt interact to produce a smooth, oily composition which readily coats the skin and carries the remaining components of the composition. While not wishing to be bound by speculation, the inventor theorizes that the ascorbic acid and/or the salts interact with one another, and possibly chelate the amino acid or other carboxylic acid to stabilize it and moderate its effects. Urea is one further ingredient which has been found beneficial in the base composition. The urea may be derived from the amino acid based composition itself or may be added in addition. The urea functions as a skin moisturizer and softener and facilitates penetration of various components of the composition into the skin.

The ascorbic acid is typically present in an amount of approximately 0.5 to 10%, and the mineral salts are typically present in amounts of between 1 and 20%. In those instances where urea is included in the composition, it is typically present in an amount of up to 5% and most preferably about 1%.

It is thus to be appreciated that in accord with a first aspect of the present invention, there are provided therapeutic compositions for the treatment of the skin, and methods for their fabrication, wherein the compositions include alpha amino carboxylic acids, and most preferably alpha amino dicarboxylic acids such as aspartic and glutamic acid. The amino acids are preferably solubilized by the action of a strong acid, and the resultant composition neutralized to a therapeutically effective pH with a base such as urea or the like. Yet other ingredients may be further included in the compositions as detailed above. In accord with another aspect of the present invention, there is provided a carrier base which includes ascorbic acid and mineral salts. The base may be used together with the amino acid compositions, or with prior art compositions such as hydroxy acids.

Therefore, it is to be understood that in view of the teaching presented herein, numerous modifications and variations of the present invention may be implemented. The foregoing discussion and description are illustrative of some particular embodiments, but are not meant to be limitations upon the practice thereof. It is the following claims, including all equivalents, which define the scope of the invention.

What is claimed is:

1. A composition for the treatment of skin, said composition consisting essentially of:
   an alpha amino acid;
   a pharmaceutically acceptable carrier, said composition having a pH in the range of 0.5–5; and
   a strong acid, in an amount sufficient to solubilize said alpha amino acid, and a base, in an amount sufficient to maintain said composition at said pH of 0.5–5.

2. A composition as in claim 1, wherein said alpha amino acid comprises an alpha amino dicarboxylic acid.

3. A composition as in claim 2, wherein said alpha amino dicarboxylic acid is selected from the group consisting of aspartic acid, glutamic acid, and combinations thereof.

4. A composition as in claim 1, wherein said strong acid is selected from the group consisting of a halocarboxylic acid, hydrochloric acid, perchloric acid and combinations thereof.

5. A composition as in claim 1, wherein said base is selected from the group consisting of urea, purines, amines, ammonium hydroxide, alkali metal hydroxides, and combinations thereof.

6. A composition as in claim 1, wherein the concentration of said alpha amino acid is, on a weight basis, in the range of 0.5–30%.

7. A composition for the treatment of skin consisting essentially of, on a weight basis:
- 0.5–20% of a member selected from the group consisting of aspartic acid, glutamic acid, and combinations thereof;
- 0.5–20% of a strong acid selected from the group consisting of halocarboxylic acids, hydrochloric acid, sulfuric acid, and combinations thereof;
- a base, in an amount sufficient to adjust the pH of said composition to a value in the range of 0.5–5;
- 0–5% of an inorganic salt of an element selected from Group I or Group II of the periodic table;
- 0–5% ascorbic acid; and
- a pharmaceutically acceptable carrier.

8. A composition for the treatment of skin, said composition consisting essentially of:
- an alpha amino acid;
- a pharmaceutically acceptable carrier, said composition having a pH in the range of 0.5–5; and
- a strong acid selected from the group consisting of a halocarboxylic acid, hydrochloric acid, perchloric acid and combinations thereof, and a base, in an amount sufficient to maintain said composition at said pH of 0.5–5.

9. A composition for the treatment of skin, said composition consisting essentially of:
- an alpha amino acid;
- a pharmaceutically acceptable carrier, said composition having a pH in the range of 0.5–5; and
- a strong acid, in an amount sufficient to solubilize said alpha amino acid, and a base selected from the group consisting of urea, purines, amines, ammonium hydroxide, alkali metal hydroxides, and combinations thereof, in an amount sufficient to maintain said composition at said pH of 0.5–5.

* * * * *